(12) United States Patent
Zimmers et al.

(10) Patent No.: US 8,449,616 B2
(45) Date of Patent: May 28, 2013

(54) APPARATUS FOR REPLACING A DAMAGED SPINAL DISC

(75) Inventors: Kari B. Zimmers, Solon, OH (US);
James E. Barber, Avon, OH (US);
Keith Duke, Cleveland, OH (US);
James M. Kuras, Macedonia, OH (US);
Rebecca Blice, Akron, OH (US); Tawny Bragg, Chicago, IL (US); Edward Benzel, Gate Mills, OH (US); Isador Lieberman, Plano, TX (US); E. Raymond Ross, Cheshire (GB)

(73) Assignee: Axiomed Spine Corporation, Garfield Heights, OH (US)

( * ) Notice: Subject to any disclaimer, the term of this patent is extended or adjusted under 35 U.S.C. 154(b) by 115 days.

(21) Appl. No.: 13/047,857

(22) Filed: Mar. 15, 2011

(65) Prior Publication Data

US 2012/0239149 A1    Sep. 20, 2012

(51) Int. Cl.
*A61F 2/44* (2006.01)
(52) U.S. Cl.
USPC ............................................. 623/17.16
(58) Field of Classification Search
CPC ........................................................ A61F 2/44
USPC .................................... 623/17.11–17.16
See application file for complete search history.

(56) References Cited

U.S. PATENT DOCUMENTS

| | | | |
|---|---|---|---|
| 4,863,477 A * | 9/1989 | Monson | 623/17.12 |
| 5,534,030 A | 7/1996 | Navarro et al. | |
| 5,824,094 A * | 10/1998 | Serhan et al. | 623/17.16 |
| 6,132,465 A * | 10/2000 | Ray et al. | 623/17.16 |
| 6,162,252 A * | 12/2000 | Kuras et al. | 623/17.16 |
| 6,533,818 B1 | 3/2003 | Weber et al. | |
| 6,582,468 B1 * | 6/2003 | Gauchet | 623/17.16 |
| 6,607,558 B2 | 8/2003 | Kuras | |
| 7,128,761 B2 | 10/2006 | Kuras et al. | |
| 7,156,848 B2 * | 1/2007 | Ferree | 606/261 |
| 7,169,181 B2 * | 1/2007 | Kuras | 623/17.11 |
| 7,618,459 B2 | 11/2009 | Justin et al. | |
| 7,695,517 B2 | 4/2010 | Benzel et al. | |
| 2002/0035400 A1 | 3/2002 | Bryan et al. | |
| 2006/0149273 A1 | 7/2006 | Ross et al. | |
| 2010/0010634 A1 * | 1/2010 | Binotto | 623/17.16 |

* cited by examiner

*Primary Examiner* — Pedro Philogene
(74) *Attorney, Agent, or Firm* — Tarolli, Sundheim, Covell & Tummino LLP (57) ABSTRACT

An apparatus for replacing a damaged spinal disc in a spinal column includes a first retaining device having an outer surface engageable with a first vertebra of the spinal column and an inner surface. A second retaining device has an outer surface engageable with a second vertebra of the spinal column and an inner surface. A resilient core has a first surface and a second surface. The first surface engages the inner surface of the first retaining device. The second surface engages the inner surface of the second retaining device. The resilient core has a tapered radially outer surface extending from adjacent the first surface to adjacent the second surface. The first retaining device may have a flange extending toward the second retaining device. A concave surface may extend between the first surface and the radially outer surface. The concave surface of the core may engage the flange when the apparatus is free of a load.

29 Claims, 6 Drawing Sheets

APPARATUS FOR REPLACING A DAMAGED SPINAL DISC

FIELD OF INVENTION

The present invention relates to an apparatus for replacing a damaged spinal disc in a spinal column, and more specifically, to an apparatus having a resilient core for replacing a damaged spinal disc in a spinal column.

BACKGROUND OF THE INVENTION

A known artificial disc is disclosed in U.S. Pat. No. 7,169, 181. U.S. Pat. No. 7,169,181 discloses an artificial disc having upper and lower retaining members and an elastomeric core. The upper and lower surfaces of the elastomeric core have recesses. The core deflects into the recess when the upper and lower retaining members move relative to each other.

SUMMARY OF THE INVENTION

The present invention relates to an apparatus for replacing a damaged spinal disc in a spinal column. The apparatus includes a first retaining device having an outer surface engageable with a first vertebra of the spinal column and an inner surface. A second retaining device has an outer surface engageable with a second vertebra of the spinal column and an inner surface. A resilient core has a first surface and a second surface. The first surface engages the inner surface of the first retaining device. The second surface engages the inner surface of the second retaining device. The resilient core has a tapered radially outer surface extending from adjacent the first surface to adjacent the second surface.

In another aspect of the present invention an apparatus for replacing a damaged spinal disc in a spinal column includes a first retaining device having an outer surface engageable with a first vertebra of the spinal column and an inner surface. A second retaining device has an outer surface engageable with a second vertebra of the spinal column and an inner surface. The first retaining device has a flange extending toward the second retaining device. A resilient core has a first surface, a second surface and a radially outer surface extending between the first and second surfaces. The first surface engages the inner surface of the first retaining device. The second surface engages the inner surface of the second retaining device. A concave surface extends between the first surface and the radially outer surface. The concave surface of the core engages the flange when the apparatus is free of a load.

BRIEF DESCRIPTION OF THE DRAWINGS

The foregoing and other features of the present invention will become apparent to one skilled in the art to which the present invention relates upon consideration of the following description of the invention with reference to the accompanying drawings, in which.

DESCRIPTION OF AN EXEMPLARY EMBODIMENT

The present invention relates to an artificial disc or prosthesis to replace a damaged or degenerated spinal disc in a spinal column of a human. FIGS. 1-8 illustrate an exemplary embodiment of an artificial disc or prosthesis 10 to replace a damaged or degenerated spinal disc in a Spinal column. The artificial disc 10 (FIG. 1) is used to replace a damaged spinal disc between adjacent upper and lower vertebrae (not shown) of a human spinal column. It is contemplated that the apparatus or artificial disc 10 may be used between cervical vertebrae of a human spinal column.

The apparatus 10 (FIG. 1) includes an upper or first retaining device 20, a lower or second retaining device 80 and a resilient core 120 interposed between and adhered to the retaining devices. The terms "upper" and "lower" are used herein with reference to the orientation of the apparatus 10 when in the human body.

Figure 1:
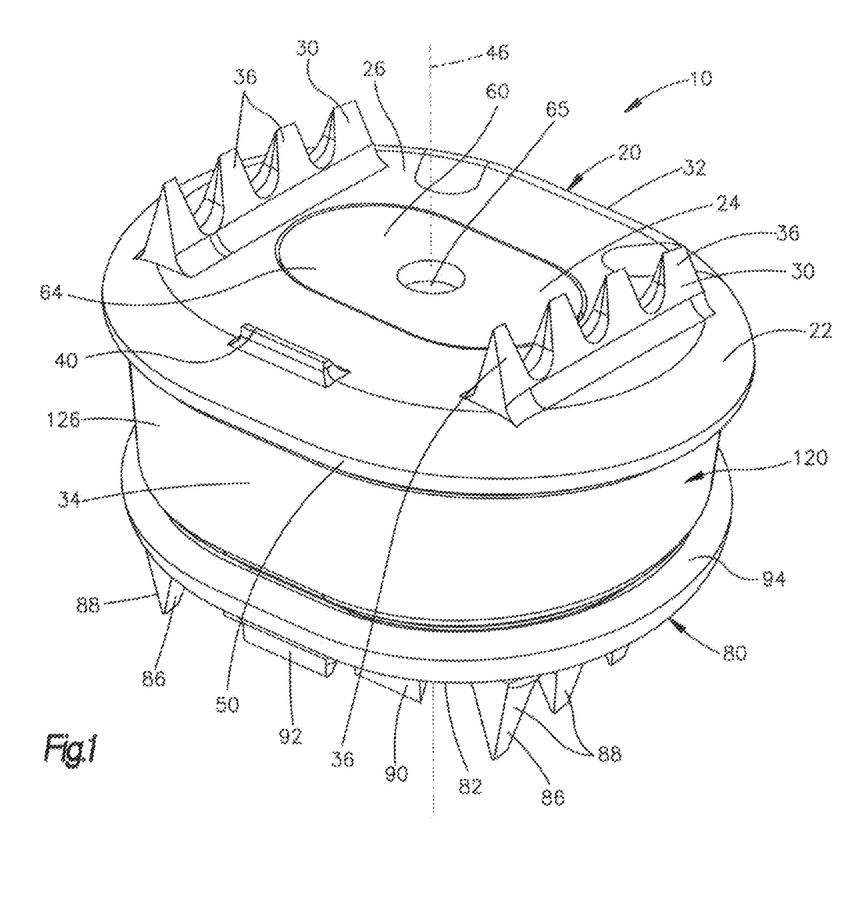
FIG. 1 is a schematic pictorial view of an apparatus to replace a damaged spinal disc constructed in accordance with the present invention.
Figure 2:
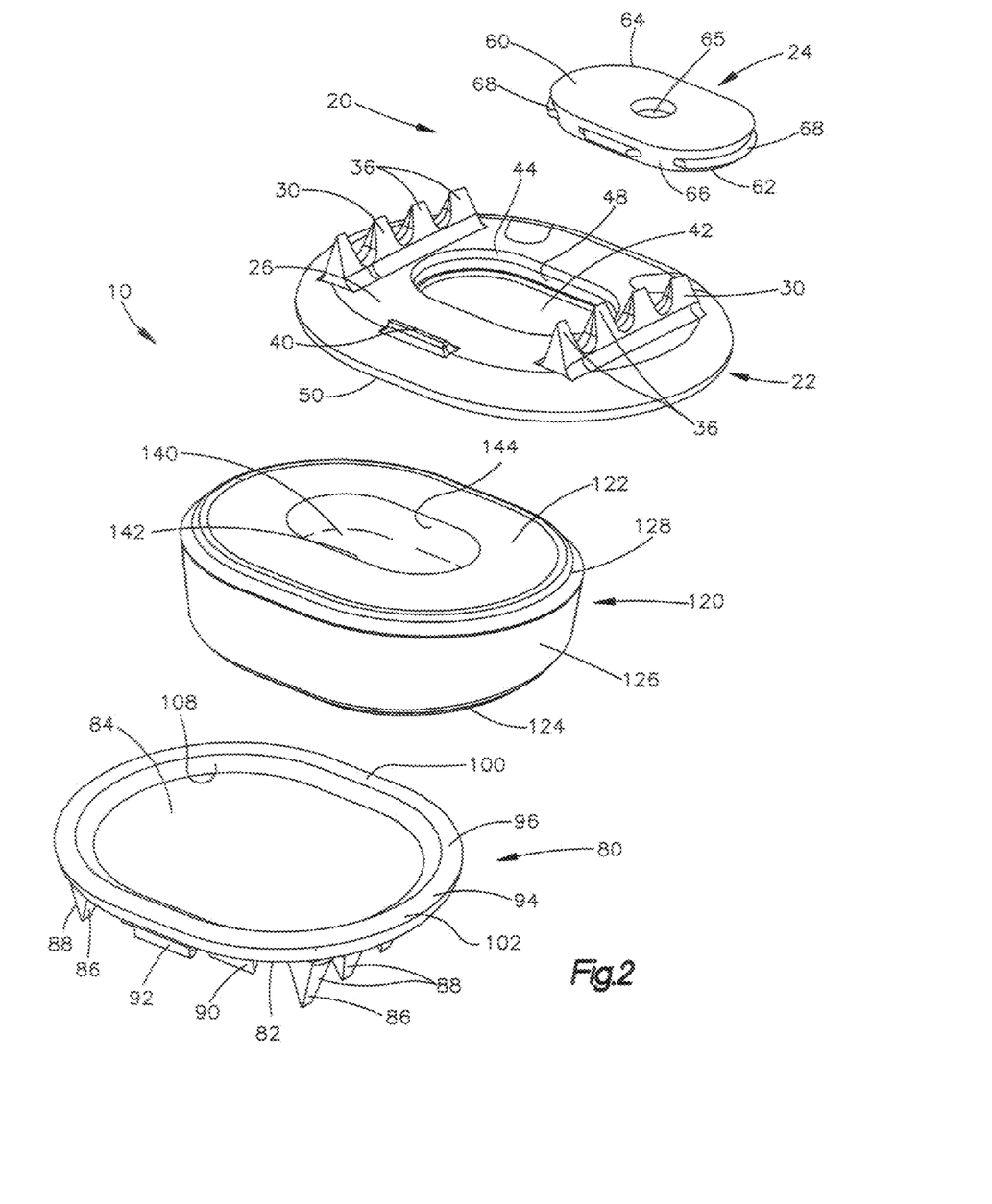
FIG. 2 is an exploded view of the apparatus of FIG. 1.
Figure 3:
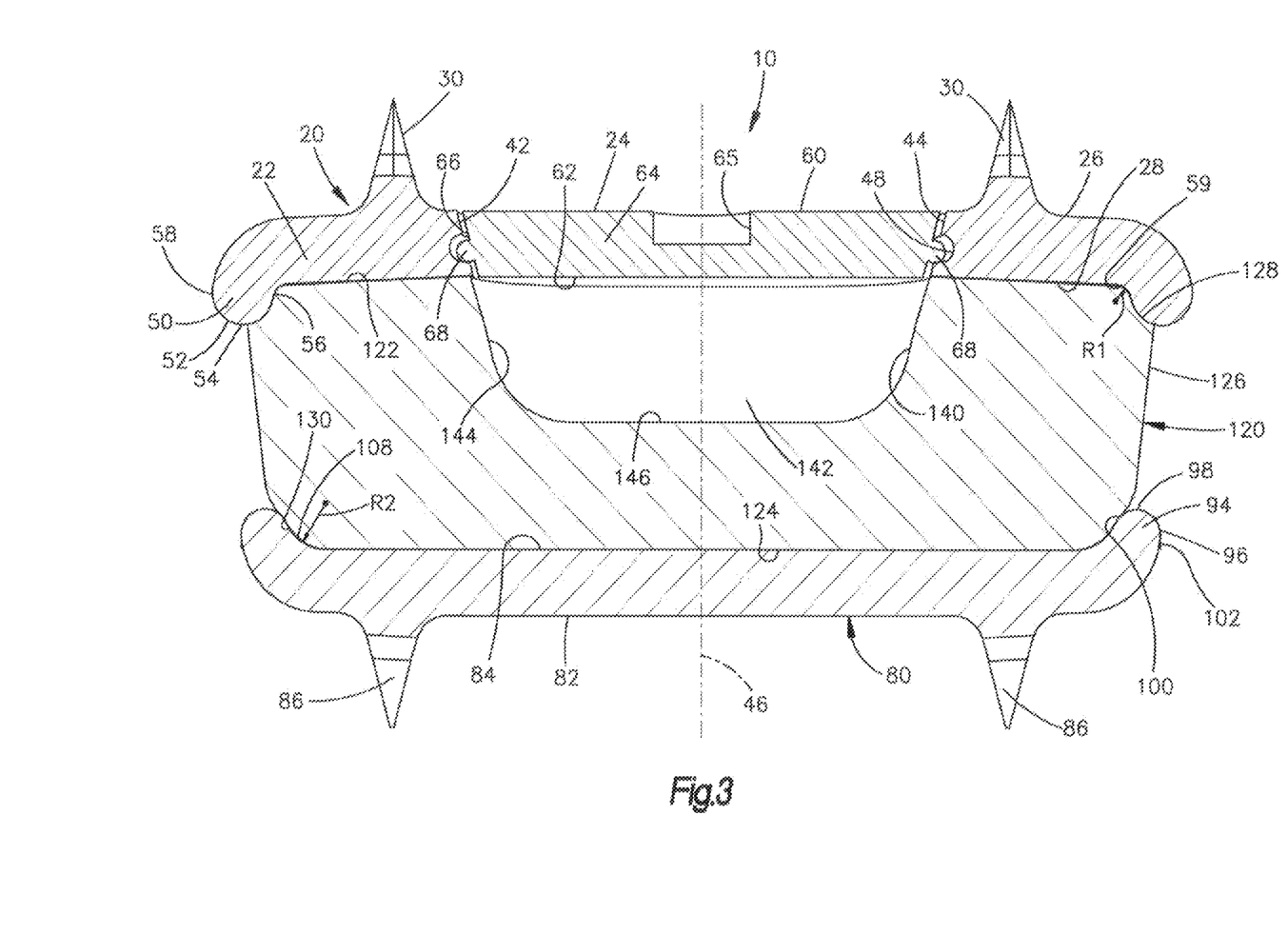
FIG. 3 is a sectional view of the apparatus of FIG. 1.

The upper retaining device 20 includes an upper or first retaining ring or member 22 and an end cap 24. The upper retaining member 22 is rigid, and made of a biocompatible material such as a biocompatible metal or polymer. It is contemplated that the upper retaining member 22 could be made of a titanium alloy. The upper retaining member 22 has an outer or upper surface 26 engageable with a vertebra. An inner surface 28 of the upper retaining member 22 is affixed or bonded to the resilient core 120. It is contemplated that the inner surface 28 may be concave and/or have beads (not shown) sintered on the inner surface or a texture (not shown) etched onto the inner surface to help connect the upper retaining member 22 to the core 120.

A plurality of ribs 30 (FIGS. 1-2) extend from the outer surface 26. Although the upper retaining member 22 is shown as having two ribs 30, it is contemplated that the upper retaining member may have any number of ribs 30. The ribs 30 extend generally parallel to each other from a posterior side 32 of the disc 10 to an anterior side 34 of the disc. It is contemplated that the ribs 30 may extend in any desired direction. Each of the ribs 30 has a plurality of projections 36. Each rib 30 is shown as having four projections 36, although the ribs may have any desired number of projections. The direction in which the ribs 30 extend may be determined by the direction of insertion of the disc 10. The ribs 30 and projections 36 engage the vertebra to retain the apparatus 10 in position between the vertebrae A tool engaging projection 40 also extends from the outer surface 26 adjacent the anterior side 34 of the disc 10. A tool (not shown) engages the projection 40 to hold the apparatus 10 during insertion of the apparatus between the vertebrae. The outer surface 26 may also have beads (not shown) sintered on the outer surface or a texture (not shown) etched onto the outer surface to further retain the apparatus 10 between the vertebrae.

An axially extending opening 42 (FIGS. 2-3 and 5) extends through the outer surface 26 and the inner surface 28 of the upper retaining member 22. The opening 42 is centrally located between the ribs 30. Although the opening 42 is shown as being oval shaped, it is contemplated that the opening may have any desired size and shape. It is also contemplated that the opening 42 may not be axially located.

The upper retaining member 22 has a tapered surface 44 at least partially defining the opening 42. The tapered surface 44 (FIG. 3) tapers toward an axis 46 of the artificial disc 10 from the outer surface 26 to the inner surface 28. The tapered surface 44 is spaced from the axis 46 adjacent the outer surface 26 a first distance. The tapered surface 44 is spaced from the axis 46 adjacent the inner surface 28 a second distance smaller than the first distance. A recesses or groove 48 is formed in the tapered surface 44 for connecting the end cap 24 to the retaining member 22.

The inner surface 28 (FIG. 3) of the upper retaining member 22 is affixed or bonded to the resilient core 120. The upper retaining member 22 includes a peripheral flange portion 50 extending toward the lower retaining device 80. The flange 50 encircles the core 120. The flange 50 (FIGS. 3-4) has a convex suffice 52 with a lower most point or apex 54 facing toward the lower retaining device 80. A radially inner portion 56 of the convex surface 52 extends from the inner surface 28 to the apex 54 on the flange 50. A radially outer portion 58 of the convex surface 52 extends from the apex 54 upward, away from the lower retaining device 80. The core 120 engages at least the radially inner portion 56 of the convex surface 52 when no load is applied to the disc 10. The core 120 may be adhered or bonded to the radially inner portion 56 of the convex surface. It is contemplated that the core 120 may engage the apex 54 and/or the radially outer portion 58 of the convex surface 52 when no load is applied to the disc 10. A concave surface 59 extends from the inner surface 28 to the convex surface 52 of the flange 50 The concave surface 59 has a first radius of curvature R1.

It is contemplated that the inner surface 28 may be concave. It is also contemplated that a portion of the inner surface 28 adjacent the opening 42 may be spaced from the core 120 until a predetermined load is applied to the apparatus 10. When the predetermined load is applied to the apparatus 10, the core 120 deflects into engagement with the portion of the inner surface 28 adjacent the opening 42. When the core 120 engages the portion of the inner surface 28 adjacent the opening 42, the core stiffens since further deflection of the core is restricted by the retaining member 22.

The end cap 24 (FIGS. 1-3) extends into the opening 42 in the retaining member 22. The end cap 24 is rigid and made of a biocompatible material such as a biocompatible metal or polymer. It is contemplated that the end cap 24 could be made of a titanium alloy. The end cap 24 has an outer surface 60 that faces the vertebra. The outer surface 60 may have beads (not shown) sintered on the outer surface or a texture (not shown) etched onto the outer surface to further retain the disc 10 between the vertebrae. An inner surface 62 of the end cap 24 faces the resilient core 120.

The end cap 24 (FIGS. 1-3 and 6) includes a generally oval body 64. The body 64 includes a recess 65 in the outer surface 60. A tool (not shown) extends into the recess 65 for connecting the end cap 24 to the retaining member 22. Although the body 64 of the end cap 24 is shown as being oval, it is contemplated that the body 64 may have any desired configuration that permits the cap 24 to slide into the opening 42 in the retaining member 22.

Figure 6:
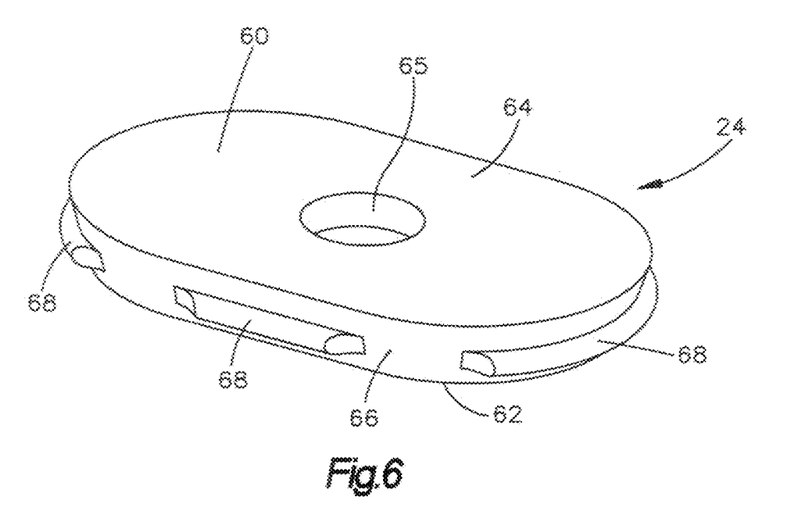
FIG. 6 is a pictorial view of an end cap of the apparatus of FIG. 1.

The body 64 of the end cap 24 has a radially outer tapered surface 66. The radially outer surface 66 on the end cap 24 may engage the tapered surface 44 on the upper retaining member 22 when the end cap is in the opening 42. A plurality of tabs 68 extend radially outwardly from the outer tapered surface 66. The tabs 68 snap into the recess or groove 48 in the tapered surface 44 of the upper retaining member 22 to connect the end cap 24 to the retaining member. The tabs 68 may permit relative movement between the end cap 24 and the retaining member 22 while retaining the end cap in the opening 42.

The lower retaining device 80 (FIGS. 2-3 and 7-8) is rigid and made from the same material as the upper retaining member 22, such as a titanium alloy. The lower retaining device 80 has an outer surface 82 engageable with a vertebra. An inner surface 84 of the lower retaining device 80 is affixed or bonded to the resilient core 120. It is contemplated that the inner surface 84 may have beads (not shown) sintered on the inner surface or a texture (not shown) etched onto the inner surface to help connect the lower retaining device 80 to the core 120.

A plurality of ribs 86 (FIG. 7) extend from the outer surface 82. Although the lower retaining device 80 is shown as having two ribs 86, it is contemplated that the lower retaining device may have any number of ribs 86. The ribs 86 extend generally parallel to each other from the posterior side 32 of the disc 10 to the anterior side 34 of the disc. It is contemplated that the ribs 86 may extend in any desired direction. Each of the ribs 86 has a plurality of projections 88. Each rib 86 is shown as having four projections 88, although the ribs may have any desired number of projections. The direction in which the ribs 86 extend is determined by the direction of insertion of the disc 10. The ribs 86 and projections 88 engage the vertebra to retain the apparatus 10 in position between the vertebrae.

Figure 7:
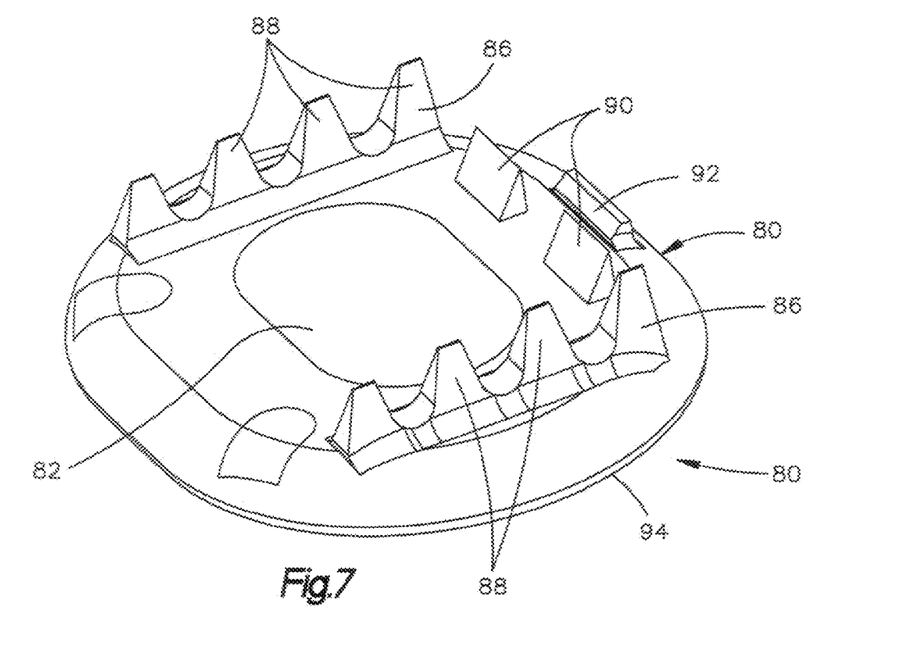
FIG. 7 is a schematic pictorial view of a lower retaining device of the apparatus of FIG. 1 showing an outer surface of the lower retaining device.
Figure 8:
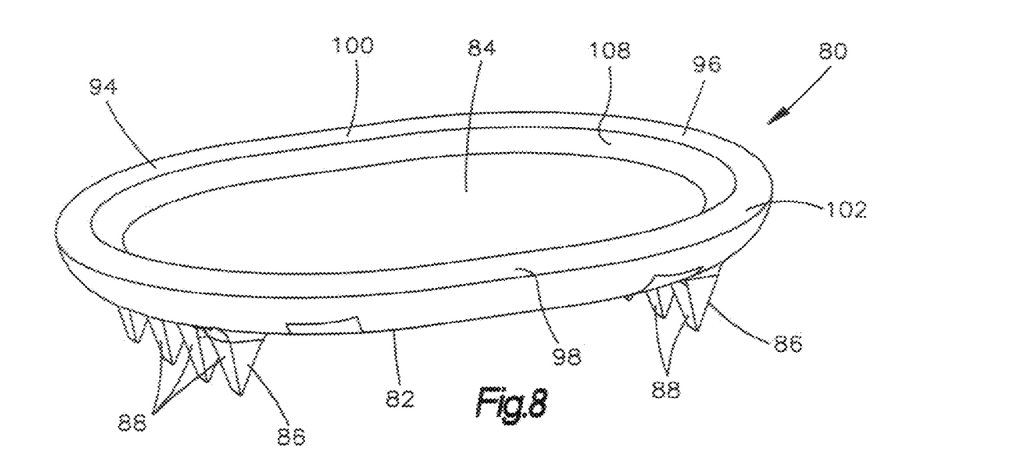
FIG. 8 is a schematic pictorial view of the lower retaining device of FIG. 7 showing an inner surface of the lower retaining device.

The outer surface 82 of the lower retaining device 80 also includes two triangular shaped projections 90. The triangular shaped projections 90 are located near the anterior side 34 of the disc 10 between the ribs 86. The projections 90 also engage the vertebra to retain the disc 10 in position between the vertebrae.

A tool engaging projection 92 extends from the outer surface 82 adjacent the anterior side 34 of the disc 10. The tool engaging projection 92 is located closer to the anterior side 34 than the triangular shaped projections 90. A tool (not shown) engages the projection 92 to hold the apparatus 10 during insertion of the apparatus between the vertebrae. The outer surface 82 may also have beads (not shown) sintered on the outer surface or a texture (not shown) etched onto the outer surface to further retain the apparatus 10 between the vertebrae.

The inner surface 84 (FIGS. 2-4 and 8) of the lower retaining device 80 is affixed or bonded to the resilient core 120. The lower retaining device 80 includes a peripheral flange portion 94 extending toward the upper retaining device 20. The flange 94 encircles the core 120. The flange 94 (FIG. 4), has a convex surface 96 with an upper most point or apex 98 facing toward the upper retaining device 20. A radially inner portion 100 of the convex surface 96 extends from the inner surface 84 to the apex 98 on the flange 94. A radially outer portion 102 of the convex surface 96 extends from the upper most point 98 downward, away from the upper retaining device 20. The core 120 engages at least the radially inner portion 100 of the convex surface 96 when no load is applied to the disc 10. The core 120 may be adhered or bonded to the radially inner portion 100 of the convex surface 96. It is contemplated that the core 120 may engage the apex 98 and/or the radially outer portion 102 of the convex surface 96 when no load is applied to the disc 10.

Figure 4:
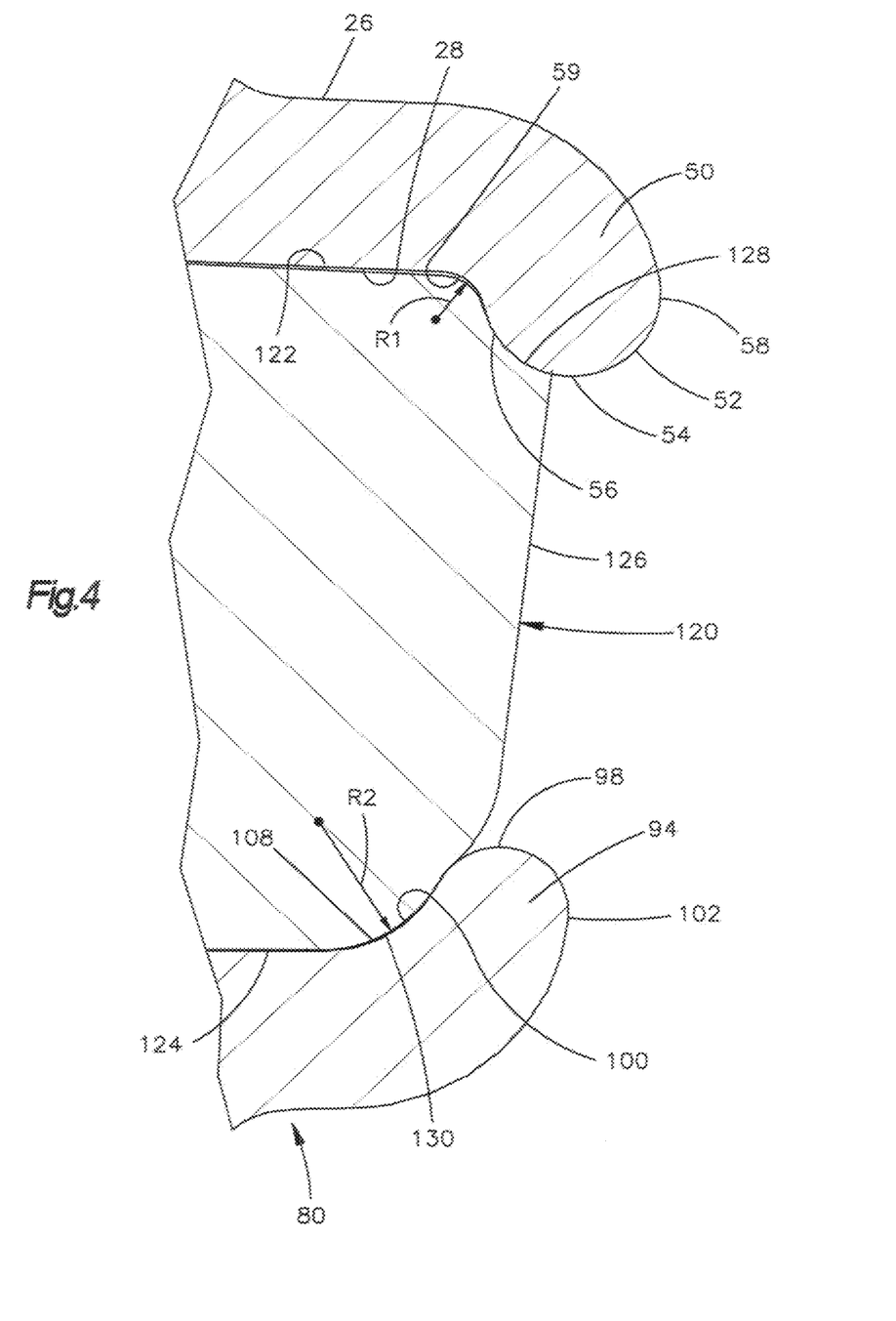
FIG. 4 is an enlarged sectional view of a portion of the apparatus of FIG. 3.
Figure 5:
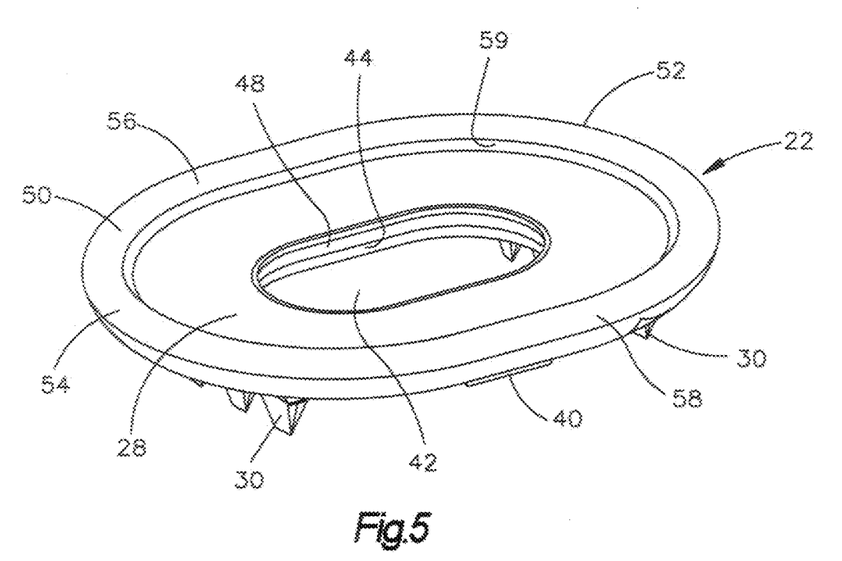
FIG. 5 is a schematic pictorial view of a retaining member of the apparatus of FIG. 1 showing an inner surface of the retaining member.

A concave surface 108 extends from the inner surface 84 to the convex surface 96 of the flange 94. The concave surface 108 has a second radius of curvature R2. The second radius of curvature R2 of the concave surface 108 is larger than the radius of curvature R1 of the concave surface of the upper retaining member 22.

It is contemplated that the inner surface 84 of the retaining device 80 may be concave. It is also contemplated that portion of the inner surface. 84 may be spaced from the core 120 until a predetermined load is applied to the apparatus 10. When the predetermined load is applied to the apparatus 10, the core 120 deflects into engagement with the portion of the inner surface 84 spaced from the core 120. When the core 120 engages the portion of the inner surface 84 spaced from the core, the core stiffens since further deflection of the core is restricted by the retaining member 80.

The resilient core 120 (FIGS. 1-3) is one-piece and may be made of a urethane silicone copolymer. The resilient core 120 may be adhered or bonded to the upper and lower retaining devices 20 and 80 in any manner known in the art. It is contemplated that the resilient core 120 could be insert molded, transfer molded or injection molded between the upper and lower retaining devices 20 and 80. The core 120 may be molded between the upper and lower retaining devices 20 and 80 by injecting the material for the core through the opening 42 in the upper retaining member 22.

The resilient core 120 may be wedge shaped. The upper retaining device 20 is spaced from the lower retaining device 80 a first distance adjacent the posterior side 32 of the disc 10. The upper retaining device 20 is spaced from the lower retaining device 80 a second distance greater than the first distance adjacent the anterior side 34 of the disc 10. It is contemplated that the upper retaining device 20 may be spaced from the lower retaining device 80 by any desired distances.

The core 120 has an upper or first surface 122. The upper surface 122 is affixed to the inner surface 28 of the upper retaining device 20. A lower or second surface 124 is affixed to the inner surface 84 of the lower retaining device 80. The upper surface 122 of the core 120 extends radially outwardly from the axis 46 a greater distance than the lower surface 124 extends radially from the axis. Accordingly, the upper surface 122 extends over a larger area than the lower surface 124. It is contemplated that the upper and lower surfaces 122, 124 may be convex.

The core 120 includes a radially outer surface 126. An upper concave transition surface 128 (FIG. 4) extends between the radially outer surface 126 and the upper surface 122. A lower concave transition surface 130 extends between the radially outer surface 126 and the lower surface 124. The upper concave transition surface 128 engages the radially inner portion 56 of the convex surface 52 on the flange 50 of the upper retaining device 20. The lower concave transition surface 130 engages the radially inner portion 100 of the flange 94 on the lower retaining device 80.

The radially outer surface 126 (FIGS. 3-4) tapers from the upper concave transition surface 128 to the lower concave transition surface 130. Accordingly, the radially outer surface 126 tapers from adjacent the upper surface 122 to adjacent the lower surface 124. The tapered surface 126 tapers continuously toward the axis 46 of the disc 10 from adjacent the upper surface 122 and the upper concave surface 128 to the lower concave surface 130 and adjacent the lower surface 124. The radially outer surface 126 is spaced a first distance from the axis 46 of the artificial disc 10 adjacent upper surface 122 and the upper concave transition surface 128. The radially outer surface 126 is spaced from the axis 46 of the artificial disc 10 adjacent the lower surface 124 and the lower concave transition surface 130 a second distance smaller than the first distance. Accordingly, the core 120 has a trapezoidal shaped cross-section. It is contemplated that the core may not include the concave transition surfaces 128 and 130. If the core 120 does not include the concave transition surfaces 128, 130, the radially outer surface 126 would taper from the upper surface 122 to the lower surface 124. Although the radially outer surface 126 is shown as having the same angle of taper around the circumference, it is contemplated that the radially outer surface may have different angles of taper on different sides of the core 120.

The core 120 (FIGS. 2-3) has an oval shaped recess 140 extending from the upper surface 122 toward the lower surface 124. The recess 140 at least partially defines an empty space 142 that extends from the upper surface 122 toward the lower surface 124. A tapered surface 144 extends from the upper surface 122 to a surface 146 that extends transverse to the axis 46 of the disc 10. The surfaces 144 and 146 define the concave recess 140 in the upper surface that is coaxial with the disc 10 and defines the empty space 142. The tapered surface 144 tapers toward the axis 46 of the disc 10 from the upper surface 122 to the surface 146. It is contemplated that the tapered surface 144 may have different angles of taper on different sides of the recess 140. The resilient core 120 may deflect into the empty space 142 defined by the recess 146 upon relative movement between the upper and lower retaining devices 20 and 80. The core 120 expends energy when the core deflects into the empty space 142 to limit the amount of stress in the core.

Although the core 120 is described as having an oval shaped recess, it is contemplated that the recess 140 may have any desired shape or depth and be in any desired location in the upper surface 122. The core 120 may also include a recess extending from the lower surface 124 toward the upper surface 122. It is also contemplated that the core 120 may have any number of recesses.

It will be understood that the above description of the present invention is susceptible to various modifications, changes and adaptations, and the same are intended to be comprehended within the meaning and range of equivalents of the appended claims. The presently disclosed embodiments are considered in all respects to be illustrative, and not restrictive. The scope of the invention is indicated by the appended claims, rather than the foregoing description, and all changes that come within the meaning and range of equivalence thereof are intended to be embraced therein.

Having described the invention, we claim:

1. An apparatus for replacing a damaged spinal disc in a spinal column, said apparatus comprising:
   a first retaining device having an outer surface engageable with a first vertebra of the spinal column and an inner surface;
   a second retaining device having an outer surface engageable with a second vertebra of the spinal column and an inner surface; and
   a resilient core having a first surface and a second surface, said first surface engaging said inner surface of said first retaining device, said second surface engaging said inner surface of said second retaining device, said first surface extending radially outwardly from an axis of said apparatus a greater distance than said second surface extends radially outwardly from the axis, said resilient core having a tapered radially outer surface extending from adjacent said first surface to adjacent said second surface.

2. An apparatus as defined in claim 1 wherein said first surface of said resilient core is fixedly attached to said inner surface of said first retaining device, said second surface of said resilient core being fixedly attached to said inner surface of said second retaining device.

3. An apparatus as defined in claim 1 wherein said core includes a concave surface extending from adjacent said first surface, towards said second surface, and to said radially outer surface, said first retaining device including a flange extending toward said second retaining device, said flange engaging said concave surface of said core when said apparatus is free of a load.

4. An apparatus as defined in claim 3 wherein said flange includes a convex surface with a radially inner portion extending between said inner surface of said first retaining device and an apex of said flange, said radially inner portion of said convex surface engaging said concave surface of said core when said apparatus is free of a load.

5. An apparatus as defined in claim 1 wherein said core includes a first concave surface extending between said first surface and said radially outer surface, said first retaining device including a flange extending toward said second retaining device, said flange engaging said first concave surface of said core when said apparatus is free of a load, said core including a second concave surface extending between said second surface and said radially outer surface, said second retaining device including a flange extending toward said first retaining device, said flange of said second retaining device engaging said second concave surface of said core when said apparatus is free of a load.

6. An apparatus as defined in claim 5 wherein said flange of said first retaining device includes a convex surface with a radially inner portion extending between said inner surface of said first retaining device and an apex of said flange, said radially inner portion of said convex surface engaging said first concave surface of said core when said apparatus is free of a load, said flange of said second retaining device including a convex surface with a radially inner portion extending between said inner surface of said second retaining device and an apex of said flange, said radially inner portion of said convex surface of said second retaining device engaging said second concave surface of said core when said apparatus is free of a load.

7. An apparatus as defined in claim 1 wherein said first retaining device includes a retaining member and an end cap, said end cap extending into an opening extending through said inner and outer surfaces of said retaining member.

8. An apparatus as defined in claim 7 wherein said end cap is snapped into the opening in said retaining member.

9. An apparatus as defined in claim 1 wherein said resilient core has a surface extending from one of said first and second surfaces toward another of said first and second surfaces and at least partially defining an empty space extending from said one of said first and second surfaces.

10. An apparatus as defined in claim 9 wherein one of said first and second surfaces includes a recess defining said empty space.

11. An apparatus as defined in claim 9 wherein said surface at least partially defining the empty space extends from said first surface of said core, said radially outer surface being spaced a first distance from an axis of said apparatus adjacent said first surface of said core, said radially outer surface being spaced a second distance smaller than said first distance from said axis of said apparatus adjacent said second surface of said core.

12. An apparatus as defined in claim 1 wherein said core has a trapezoidal shaped cross-section.

13. An apparatus as defined in claim 1 wherein said first surface of said core extends over a larger area than said second surface of said core.

14. An apparatus as defined in claim 1 wherein said first retaining device includes a flange extending toward said second retaining device, said first retaining device having a first concave surface extending between said inner surface of said first retaining device and said flange, said first concave surface having a first radius of curvature, said second retaining device including a flange extending toward said first retaining device, said second retaining device having a second concave surface extending between said inner surface of said second retaining device and said flange, said second concave surface having a second radius of curvature different than said first radius of curvature.

15. An apparatus as defined in claim 14 wherein said flange of said first retaining device includes a convex surface with a radially inner portion extending between said first concave surface of said first retaining device and an apex of said flange, said radially inner portion of said convex surface engaging a first concave surface of said core when said apparatus is free of a load, said flange of said second retaining device including a convex surface with a radially inner portion extending between said second concave surface and an apex of said flange, said radially inner portion of said convex surface of said second retaining device engaging a second concave surface of said core when said apparatus is free of a load.

16. An apparatus as defined in claim 14 wherein said first surface of said core includes a recess defining an empty space, said first radius of curvature of said first concave surface being smaller than said second radius of curvature of said second concave surface of said second retaining device.

17. An apparatus as defined in claim 16 wherein said radially outer surface tapers continuously between said first and second concave surfaces of said resilient core.

18. An apparatus for replacing a damaged spinal disc in a spinal column, said apparatus comprising:
a first retaining device having an outer surface engageable with a first vertebra of the spinal column and an inner surface;
a second retaining device having an outer surface engageable with a second vertebra of the spinal column and an inner surface;
said first retaining device having a flange extending toward said second retaining device; and
a resilient core having a first surface, a second surface and a radially outer surface extending between said first and second surfaces, said first surface engaging said inner surface of said first retaining device, said second surface engaging said inner surface of said second retaining device, a concave surface extending from adjacent said first surface, towards said second surface, and to said radially outer surface, said concave surface of said core engaging said flange when said apparatus is free of a load, wherein said flange includes a convex surface with a radially inner portion extending between said inner surface of said first retaining device and an apex of said flange, said radially inner portion of said convex surface engaging said concave surface of said core when said apparatus is free of a load.

19. An apparatus as defined in claim 18 wherein said first surface of said resilient core is fixedly attached to said inner surface of said first retaining device, said second surface of said resilient core being fixedly attached to said inner surface of said second retaining device.

20. An apparatus as defined in claim 18 wherein said second retaining device includes a flange extending toward said first retaining device, said core including a concave surface extending between said second surface and said radially outer surface, said concave surface of said core extending between said second surface and said radially outer surface engaging said flange of said second retaining device when said apparatus is free of a load.

21. An apparatus as defined in claim 20 wherein said flange of said first retaining device includes a convex surface with a radially inner portion extending between said inner surface of said first retaining device and an apex of said flange, said radially inner portion of said convex surface engaging said concave surface extending between said first surface and said radially outer surface when said apparatus is free of a load, said flange of said second retaining device including a convex surface with a radially inner portion extending between inner surface of said second retaining device and an apex of said flange, said radially inner portion of said convex surface of said second retaining device engaging said concave surface extending between said second surface and said radially outer surface when said apparatus is free of a load.

22. An apparatus as defined in claim 18 wherein said first retaining device includes a retaining member and an end cap, said end cap being snapped into an opening extending through said inner and outer surfaces of said retaining member.

23. An apparatus as defined in claim 18 wherein at least one of said first and second surfaces includes a recess defining an empty space.

24. An apparatus as defined in claim 23 wherein said first surface includes said recess, said radially outer surface being spaced a first distance from an axis of said apparatus adjacent said first surface of said core, said radially outer surface being spaced a second distance smaller than said first distance from said axis of said apparatus adjacent said second surface of said core.

25. An apparatus as defined in claim 18 wherein said core has a trapezoidal shaped cross-section.

26. An apparatus as defined in claim 18 wherein said first surface of said core extends over a larger area than said second surface of said core.

27. An apparatus as defined in claim 18 wherein said first retaining device has a first concave surface extending between said inner surface of said first retaining device and said flange, said first concave surface having a first radius of curvature, said second retaining device including a flange extending toward said first retaining device, said second retaining device having a second concave surface extending between said inner surface of said second retaining device and said flange, said second concave surface having a second radius of curvature different than said first radius of curvature.

28. An apparatus as defined in claim 27 wherein said first surface of said core includes a recess defining an empty space, said first radius of curvature of said first concave surface being smaller than said second radius of curvature of said second concave surface of said second retaining device.

29. An apparatus as defined in claim 18 wherein the first surface extends radially outwardly from an axis of the apparatus a greater distance than the second surface extends radially outwardly from the axis.

* * * * *